(12) United States Patent
Holz et al.

(10) Patent No.: US 11,672,429 B2
(45) Date of Patent: Jun. 13, 2023

(54) SENSOR DEVICE

(71) Applicant: Microsoft Technology Licensing, LLC, Redmond, WA (US)

(72) Inventors: Christian Holz, Seattle, WA (US); Eyal Ofek, Redmond, WA (US); Michael J. Sinclair, Kirkland, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 17/104,824

(22) Filed: Nov. 25, 2020

(65) Prior Publication Data

US 2021/0100459 A1 Apr. 8, 2021

Related U.S. Application Data

(63) Continuation of application No. 15/871,733, filed on Jan. 15, 2018, now Pat. No. 10,874,305.

(51) Int. Cl.
*A61B 5/02* (2006.01)
*A61B 5/00* (2006.01)
(Continued)

(52) U.S. Cl.
CPC ........ *A61B 5/02028* (2013.01); *A61B 5/0017* (2013.01); *A61B 5/0024* (2013.01);
(Continued)

(58) Field of Classification Search
CPC ... A61B 5/02028; A61B 5/0017; A61B 5/489; A61B 5/14551; A61B 5/0261; A61B 5/02416; A61B 5/02125; A61B 5/02007; A61B 5/0093; A61B 5/7221; A61B 5/6844; A61B 5/6813; A61B 5/0024;
(Continued)

(56) References Cited

U.S. PATENT DOCUMENTS

| 6,349,227 B1 | 2/2002 | Numada |
| 7,530,949 B2 | 5/2009 | Al Ali et al. |

(Continued)

FOREIGN PATENT DOCUMENTS

AU 2014200060 B2 1/2014

OTHER PUBLICATIONS

Y. Lee, H. Shin, J. Jo and Y.-K. Lee, "Development of a wristwatch-type PPG array sensor module," 2011 IEEE International Conference on Consumer Electronics—Berlin (ICCE—Berlin), 2011, pp. 168-171, doi: 10.1109/ICCE-Berlin.2011.6031811. (Year: 2011).*

(Continued)

*Primary Examiner* — Andrae S Allison
(74) *Attorney, Agent, or Firm* — Calfee, Halter & Griswold LLP

(57) ABSTRACT

A sensor device is described herein. The sensor device includes a multi-dimensional optical sensor and processing circuitry, wherein the multi-dimensional optical sensor generates images and the processing circuitry is configured to output data that is indicative of hemodynamics of a user based upon the images. The sensor device is non-invasive, and is able to be incorporated into wearable devices, thereby allowing for continuous output of the data that is indicative of the hemodynamics of the user.

20 Claims, 13 Drawing Sheets

(51) Int. Cl.
  *A61B 5/021* (2006.01)
  *A61B 5/1455* (2006.01)
  *A61B 5/024* (2006.01)
  *A61B 5/026* (2006.01)
  *A61B 5/107* (2006.01)

(52) U.S. Cl.
  CPC ........ *A61B 5/0093* (2013.01); *A61B 5/02007* (2013.01); *A61B 5/0261* (2013.01); *A61B 5/02125* (2013.01); *A61B 5/02416* (2013.01); *A61B 5/14551* (2013.01); *A61B 5/489* (2013.01); *A61B 5/6813* (2013.01); *A61B 5/6844* (2013.01); *A61B 5/7221* (2013.01); *A61B 5/0077* (2013.01); *A61B 5/021* (2013.01); *A61B 5/02108* (2013.01); *A61B 5/02427* (2013.01); *A61B 5/02438* (2013.01); *A61B 5/1075* (2013.01); *A61B 5/1076* (2013.01); *A61B 5/1079* (2013.01); *A61B 5/1455* (2013.01); *A61B 5/14552* (2013.01); *A61B 5/681* (2013.01); *A61B 5/6803* (2013.01); *A61B 5/6822* (2013.01); *A61B 5/6824* (2013.01); *A61B 5/6828* (2013.01); *A61B 5/6898* (2013.01); *A61B 5/7207* (2013.01); *A61B 2562/046* (2013.01); *A61B 2576/00* (2013.01)

(58) Field of Classification Search
  CPC . A61B 2576/00; A61B 5/6824; A61B 5/6822; A61B 5/681; A61B 5/6803; A61B 5/14552; A61B 5/1079; A61B 5/1076; A61B 5/1075; A61B 5/02438; A61B 5/02427; A61B 5/02108; A61B 5/021; A61B 5/0077; A61B 5/7207; A61B 5/6898; A61B 5/6828; A61B 5/1455; A61B 2562/046
  See application file for complete search history.

(56) References Cited

U.S. PATENT DOCUMENTS

| | | | |
|---|---|---|---|
| 7,972,266 | B2 | 7/2011 | Gobeyn et al. |
| 8,909,311 | B2 | 12/2014 | Ho et al. |
| 9,060,683 | B2 | 6/2015 | Tran |
| 9,414,780 | B2 | 8/2016 | Rhoads |
| 9,770,197 | B2 | 9/2017 | Bresch et al. |
| 9,826,940 | B1 | 11/2017 | Lengerich |
| 9,968,282 | B2 | 5/2018 | Makkapati et al. |
| 10,052,035 | B2 | 8/2018 | Martin et al. |
| 10,209,794 | B2 | 2/2019 | Wang et al. |
| 10,682,180 | B2 | 6/2020 | Taylor |
| 2005/0010119 | A1 | 1/2005 | Palti et al. |
| 2008/0292151 | A1 | 11/2008 | Kurtz et al. |
| 2009/0203998 | A1 | 8/2009 | Klinghult et al. |
| 2009/0306524 | A1* | 12/2009 | Muhlsteff .......... A61B 5/02125 600/502 |
| 2010/0204588 | A1* | 8/2010 | Kim .................. A61B 5/021 600/485 |
| 2010/0246651 | A1 | 9/2010 | Baheti et al. |
| 2011/0066381 | A1 | 3/2011 | Garudadri et al. |
| 2011/0124978 | A1 | 5/2011 | Williams |
| 2012/0215114 | A1* | 8/2012 | Gratton .............. A61B 5/02028 600/479 |
| 2013/0120106 | A1 | 5/2013 | Cauwels et al. |
| 2013/0197322 | A1* | 8/2013 | Tran .................. A61B 8/565 600/595 |
| 2014/0012142 | A1 | 1/2014 | Mestha et al. |
| 2014/0148663 | A1 | 5/2014 | Bresch et al. |
| 2014/0168167 | A1 | 6/2014 | Chou |
| 2014/0221849 | A1 | 8/2014 | Farringdon et al. |
| 2014/0336478 | A1 | 11/2014 | Segman |
| 2015/0018660 | A1 | 1/2015 | Thomson et al. |
| 2015/0018676 | A1 | 1/2015 | Barak |
| 2015/0119725 | A1 | 4/2015 | Martin et al. |
| 2015/0216484 | A1 | 8/2015 | Kasahara et al. |
| 2015/0297119 | A1 | 10/2015 | Makkapati et al. |
| 2015/0335293 | A1 | 11/2015 | Christman et al. |
| 2016/0015282 | A1* | 1/2016 | Kim .................. A61B 5/7278 600/479 |
| 2016/0034042 | A1 | 2/2016 | Joo |
| 2016/0098834 | A1 | 4/2016 | Eguchi et al. |
| 2016/0360974 | A1 | 12/2016 | Lange |
| 2017/0035359 | A1 | 2/2017 | Qiu et al. |
| 2017/0065184 | A1* | 3/2017 | Barak ............... A61B 5/02438 |
| 2017/0079591 | A1 | 3/2017 | Gruhlke et al. |
| 2017/0143249 | A1 | 5/2017 | Davis et al. |
| 2017/0156651 | A1 | 6/2017 | Arias et al. |
| 2018/0042496 | A1 | 2/2018 | Lachhman et al. |
| 2018/0055369 | A1 | 3/2018 | Burns et al. |
| 2018/0055428 | A1 | 3/2018 | Toya |
| 2018/0110450 | A1 | 4/2018 | Lamego et al. |
| 2018/0333088 | A1* | 11/2018 | Holz .................. A61B 5/1032 |
| 2018/0372714 | A1 | 12/2018 | Chen et al. |
| 2019/0008392 | A1 | 1/2019 | Wang et al. |
| 2019/0069842 | A1 | 3/2019 | Rothberg et al. |
| 2019/0216340 | A1* | 7/2019 | Holz .................. A61B 5/489 |
| 2020/0129077 | A1* | 4/2020 | Rogers ............... A61B 5/02108 |
| 2020/0305798 | A1* | 10/2020 | Ishikawa ............ A61B 5/02416 |

OTHER PUBLICATIONS

O'toole et al, Absorbance Based Light Emitting Diode Optical Sensors and Sensing Devices, Sensors 2008, 8, 2453-2479 (Year: 2008).*

Tamura et al, Wearable Photoplethysmographic Sensors—Past and Present, Electronics 2014, 3, 282-302; (Year: 2014).*

Castaneda, Denisse, et al. "A review on wearable photoplethysmography sensors and their potential future applications in health care." International journal of biosensors & bioelectronics 4.4 (2018): 195. (Year: 2018).*

"Office Action Issued in Indian Patent Application No. 202017029453", dated Apr. 26, 2022, 6 Pages.

"First Office Action Issued in Chinese Patent Application No. 201980008198.9", dated Nov. 3, 2022, 10 Pages.

"Adaptive blood pressure estimation from wearable PPG sensors using peripheral artery pulse wave velocity measurements and multi-channel blind identification of local arterial dynamics", In Proceedings of 28th Annual International Conference of the IEEE Engineering in Medicine and Biology Society, Aug. 30, 2006, pp. 3521-3524.

"Simband: A digital health device", Retrieved From <<https://www.simband.io/>>, Retrieved On: Nov. 10, 2017, 1 Page.

"Pulse Oximetry Capturing Technique", Application as Filed in U.S. Appl. No. 15/597,514, filed May 17, 2017, 26 Pages.

Chandrasekaran, et al., "Cuffless differential blood pressure estimation using smart phones", In Journal of IEEE Transactions on Biomedical Engineering, vol. 60, No. 4, Apr. 2013, pp. 1080-1089.

Constant, et al., "Pulse-Glasses: An unobtrusive, wearable HR monitor with Internet-of-Things functionality", In Proceedings of IEEE 12th International Conference on Wearable and Implantable Body Sensor Networks (BSN), Jun. 12, 2015, 5 Pages.

Holz, et al., "Glabella: Continuously Sensing Blood Pressure Behavior using an Unobtrusive Wearable Device", In Proceedings of ACM on Interactive, Mobile, Wearable and Ubiquitous Technologies, vol. 1, Issue 3, Sep. 1, 2017, 23 Pages.

Liu, et al., "Toward a Smartphone Application for Estimation of Pulse Transit Time", In Journal of Sensors, vol. 15, Oct. 27, 2015, pp. 27303-27321.

"Head-Mounted Device For Capturing Pulse Data", Application as Filed in U.S. Appl. No. 15/624,602, filed Jun. 15, 2017, 24 Pages.

Payne, et al., "Pulse transit time measured from the ECG: an unreliable marker of beat-to-beat blood pressure", In Journal of Applied Physiology, vol. 100, Issue 1, Jan. 2006, pp. 136-141.

Ramakrishna, et al., "Toward ubiquitous blood pressure monitoring via pulse transit time: theory and practice", In Journal of IEEE Transactions on Biomedical Engineering, vol. 62, Issue 8, Aug. 2015, pp. 1879-1901.

(56) References Cited

OTHER PUBLICATIONS

Gesche, et al., "Continuous blood pressure measurement by using the pulse transit time: comparison to a cuff-based method", In Journal of European Journal of Applied Physiology, vol. 112, No. 1, Jan. 1, 2012, 7 Pages.

Deakin, et al., "Accuracy of the advanced trauma life support guidelines for predicting systolic blood pressure using carotid, femoral, and radial pulses: observational study", In Proceedings of BMJ, vol. 321, Sep. 16, 2000, pp. 673-674.

Thomas, et al., "BioWatch: A wrist watch based signal acquisition system for physiological signals including blood pressure", In Proceedings of 36th Annual International Conference of the IEEE Engineering in Medicine and Biology Society, Aug. 26, 2014, pp. 2286-2289.

Vappou, et al., "Pulse wave ultrasound manometry (PWUM): Measuring central blood pressure non-invasively", In Proceedings of IEEE International Ultrasonics Symposium, Oct. 18, 2011, pp. 2122-2125.

Winokur, et al., "A Wearable Vital Signs Monitor at the Ear for Continuous Heart Rate and Pulse Transit Time Measurements", In Proceedings of IEEE Annual International Conference of the Engineering in Medicine and Biology Society, Aug. 28, 2012, pp. 2724-2727.

Withings, et al., "Body Cardio Scale", Retrieved From <<https://www.withings.com/us/en/products/body-cardio>>, Retrieved On: Nov. 10, 2017, 8 Pages.

Worthing, Tyler Richard, "Using Ultrasound To Measure Arterial Diameter For The Development Of A Wearable Blood Pressure Monitoring Device", In Master's thesis of University Of British Columbia, Oct. 2016, 114 Pages.

"Cardiio uses iPhone camera sensor to get your heart rate on the go", Retrieved From: https://gigaom.com/2012/08/09/Cardiio-uses-iphone-camera-sensor-to-get-your-heart-rate-on-the-go/, Aug. 9, 2012, 9 Pages.

"Pulse Oximeter—Heart Rate and Oxygen Monitor App", Retrieved From: https://itunes.apple.com/US/app/pulse-oximeter-heart-rate-and-oxygen-monitor-app/id775632066?mt=8, Mar. 3, 2017, 4 Pages.

"Non Final Office Action Issued in U.S. Appl. No. 15/597,514", dated Mar. 18, 2019, 14 Pages.

Freitas, Ubiratan S., "Remote Camera-based Pulse Oximetry", In Proceedings of the Sixth International Conference on eHealth, Telemedicine, and Social Medicine, Mar. 1, 2014, pp. 59-63.

Gastel, et al., "New principle for measuring arterial blood oxygenation, enabling motion-robust remote monitoring", In Journal of Scientific Reports, vol. 6, Dec. 7, 2016, pp. 1-16.

Gregoski, et al., "Development and Validation of a Smartphone Heart Rate Acquisition Application for Health Promotion and Wellness Telehealth Applications", In International Journal of Telemedicine and Applications, Jan. 1, 2012, pp. 1-8.

Guazzi, et al., "Non-contact measurement of oxygen saturation with an RGB camera", In Journal of Biomedical Optic Express, vol. 6, No. 9, Aug. 11, 2015, pp. 3320-3338.

Ovadia, Blechman, et al., "The Feasibility of Flat, Portable and Wireless Device for Non-Invasive Peripheral Oxygenation Measurement over the Entire Body", In Journal of Biomedical Science and Engineering, vol. 9, Mar. 2016, pp. 147-159.

Vashist, et al., "Commercial Smartphone-Based Devices and Smart Applications for Personalized Healthcare Monitoring and Management", In Journal of Diagnostics, vol. 4, Issue 3, Sep. 1, 2014, 22 Pages.

Wang, et al., "HemaApp: Noninvasive Blood Screening of Hemoglobin using Smartphone Cameras", In Proceedings of the ACM International Joint Conference on Pervasive and Ubiquitous Computing, Sep. 12, 2016, pp. 593-604.

"Final Office Action Issued in U.S. Appl. No. 15/597,514", dated Jul. 18, 2019, 14 Pages.

"International Search Report and Written Opinion Issued in PCT Application No. PCT/US2019/012586", dated Jul. 18, 2019, 22 Pages.

"Restriction Requirement for U.S. Appl. No. 15/871,733", dated Sep. 6, 2019, 6 Pages.

"Reply to Restriction Requirement for U.S. Appl. No. 15/871,733", filed Nov. 6, 2019, 2 Pages.

Majumder, et al. "Wearable Sensors for Remote Health Monitoring", In Sensors 2017, vol. 17, No. 130, 2017, pp. 1-45.

Fu, et al., "System design for wearable blood oxygen saturation and pulse measurement device", In Procedia Manufacturing, 2015, pp. 1187-1194.

Meyer, Francois G., "Signal Data Mining from Wearable Systems", Nov. 2010, pp. 123-146.

"Non-Final Office Action for U.S. Appl. No. 15/871,733", dated Jan. 17, 2020, 14 Pages.

"Non Final Office Action Issued In U.S. Appl. No. 15/597,514", dated Feb. 19, 2020, 15 Pages.

"Reply to Non-Final Office Action for U.S. Appl. No. 15/871,733", filed Apr. 16, 2020, 18 Pages.

"Final Office Action Issued in U.S. Appl. No. 15/597,514", dated Jun. 12, 2020, 17 Pages.

"Notice of Allowance and Fees Due for U.S. Appl. No. 15/871,733", dated Aug. 19, 2020, 9 Pages.

"Non Final Office Action Issued in U.S. Appl. No. 15/597,514", dated Nov. 10, 2020, 15 Pages.

\* cited by examiner

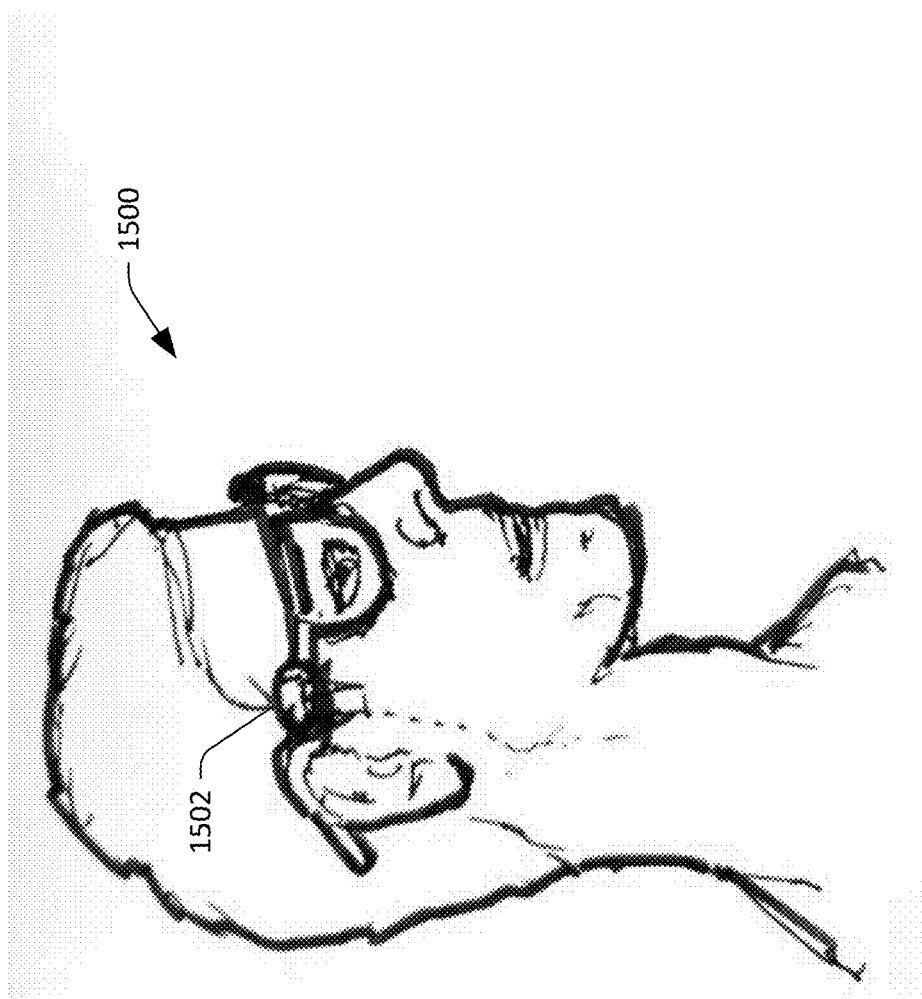

SENSOR DEVICE

RELATED APPLICATION

This application is a continuation of U.S. patent application Ser. No. 15/871,733, filed on Jan. 15, 2018, and entitled "SENSOR DEVICE", the entirety of which is incorporated herein by reference.

BACKGROUND

Systems, including clinical systems and consumer-level systems, exist that are configured with technologies that enable computation of values that are indicative of one or more metrics of health of users. For example, a clinical system can include an intra-arterial catheter line, which is configured to be placed in an artery of a user to provide direct access to blood of the user, and thus metrics pertaining to the health of the user, such as pulse, pulse waveform, blood pressure, blood oxygenation, blood volume, and cardiac output. While these clinical systems provide accurate data about the health of the user, such systems are invasive (leading to user discomfort) and are limited to use in a clinical setting (and therefore are stationary in nature).

Relatively recently, wearable devices have become quite popular, wherein these wearable devices include smart watches, fitness bands, and the like. Some of these wearable devices are configured to output data that is indicative of heart rate of a user who is wearing a wearable device. Some of these wearable devices are also configured to output data that is indicative of blood oxygenation of the user who wears a wearable device. A conventional wearable device includes one or more one-dimensional optical sensors that are positioned in proximity to an illuminator (e.g., one or more light emitting diodes (LEDs)). In operation, the illuminator directs light of certain wavelengths into the skin, and the optical sensor(s) (which are sensitive to the wavelengths) detect an amount of light not absorbed by human tissue (e.g., light that is reflected from the human tissue). Based upon magnitudes of light captured by the optical sensor(s) over time, processing circuitry in the wearable device can compute values that are indicative of the heart rate of the user and blood oxygenation of tissue of the user that lies beneath the optical sensor(s).

Because of the one-dimensional nature of each optical sensor included in a conventional wearable device, the wearable device is unable to verify that the optical sensor is properly positioned over an artery of the user. Further, due to the one-dimensional nature of sensor(s) of the conventional wearable device, the conventional wearable device is unable to detect motion artifacts based solely upon signal(s) output by the sensor(s). Put another way, the wearable device operates on the assumption that the optical sensor is located on, or close to, an artery. The optical sensor, however, not only responds to blood flowing through an artery, but also responds to environmental light changes, motion of the user (such as walking), and so on. Further, the wearable device is incapable of distinguishing between reflections from blood rushing through arteries and fluctuations stemming from other sources. For instance, when a user is walking, motion of the user may be repetitive and within a frequency range of typical heart rates. In such case, the processing circuitry may latch on to the motion frequency captured by the optical sensor, thereby reporting an inaccurate heart rate of the user. Thus, a conventional wearable device is limited to outputting values that are indicative of heart rate, and in some cases, blood oxygenation, but such values may be inaccurate due to user motion and/or environmental conditions.

There are several other metrics that are indicative of health of a patient, wherein conventional wearable devices are incapable of computing values for such metrics. These metrics include pulse transit time, blood pressure, arterial heart rate, arterial blood oxygenation, arterial pulse wave velocity, arterial diameter, arterial expansion (e.g., at different points along the artery), arterial pulse waveform, arterial blood volume, stroke volume, arterial stiffness, tissue pulse rate, and tissue oxygenation. Conventional systems for computing values for these metrics with respect to a user, however, are invasive, expensive, and/or stationary. For example, a system that determines values that are indicative of arterial heart rate and arterial blood oxygenation require use of a catheter that is inserted into the artery of a patient. With respect to arterial pulse wave velocity and pulse transit time, conventional systems have either used an echocardiographic (ECG) to approximate an amount of cardiac ejection and a photoplethysmogram (PPG) sensor placed on the wrist of a patient to compute a pulse arrival time. This system requires the user to touch a mobile device with both hands and remain still. Pulse arrival time has been shown to be subject to a factor in the cardiac cycle that is referred to as the pre-ejection period (PEP), making it unreliable in predicting blood pressure values. An alternative to circumvent the pre-ejection period is to measure the pulse transit time. Conventional systems compute the pulse transit time by using two optical PPG sensors at two locations on the same artery at different distances from the heart. These conventional systems require that the user remain stationary or wear a device that prevents normal use of the hand of the user. Other conventional systems have employed tonometers to measure pulse waves directly. Use of a tonometer, however, requires constant pressure and is associated with calibration issues. Using a tonometer to determine the arrival of a pulse at a distal location on the body of the user requires: 1) precise location of the sensor of the tonometer on the artery; and 2) adjustment to a known and calibrated pressure value when strapped to an arm of the user. Further, tonometers are highly susceptible to motion artifacts. Moreover, tonometers are one-dimensional. Accordingly, tonometers are unable to detect what object or physiological effect has caused the signal that the tonometers observe, and thus rely on continued correct placement.

Other conventional systems that have been employed to output values that are indicative of health metrics of users are ultrasound-based systems. Vascular ultrasound is a non-invasive ultrasound method that is used to examine blood circulation in the arms and legs of patients. During a vascular ultrasound, sound waves are transmitted through the tissues of the area being examined. The sound waves reflect off blood cells moving within blood vessels, thereby allowing a physician to calculate speed of the blood cells. Ultrasound-based imaging systems, however, are prohibitively expensive for consumers, and require a large device, conductive gel, and a large amount of processing power for computing images.

SUMMARY

The following is a brief summary of subject matter that is described in greater detail herein. This summary is not intended to be limiting as to the scope of the claims.

Described herein are various technologies pertaining to a sensor device that is configured to output values that are indicative of hemodynamics of a user, wherein at least some of such hemodynamics are spatial in nature. The hemodynamics about which the sensor device can output data include, but are not limited to, arterial heart rate, arterial pulse wave velocity/pulse transit time (which can be related to blood pressure), arterial expansion, arterial blood volume, pulse waveform, arterial diameter, arterial stiffness, tissue pulse rate, arterial blood oxygenation, and tissue oxygenation. It can be ascertained that data about these health metrics is usable to predict hypertension or pre-hypertension in a user, as well as other fitness and health metrics. Further, the sensor device is a non-invasive sensor device that can be positioned at a single location on a body of the human. In an example, the sensor device can be incorporated into a wearable device such as a fitness band, an armband, a neckband, etc.

The sensor device includes a multidimensional optical sensor, such as a complementary metal oxide semiconductor (CMOS) sensor that is configured to generate images having M×N pixels, where at least one of M and N are greater than or equal to one, and further wherein N and M may be equivalent to one another. The sensor device further includes illuminators (e.g., light-emitting diodes (LEDs)) that are configured to illuminate tissue beneath the surface of the skin of the user in a field of view of the multidimensional optical sensor. As blood absorbs more light in the visible spectrum than other matter in the dermis, reflections captured by the optical sensor are indicative of arteries and veins in the field of view of the optical sensor. In a nonlimiting example, the illuminators can be configured to be in contact with the surface of the skin, such that light emitted by the illuminators is coupled into the skin rather than reflected from the surface of the skin.

The sensor device also includes processing circuitry that receives images generated by the multidimensional optical sensor and computes values that are indicative of hemodynamics of the user, such as the hemodynamics presented above. In images generated by the multidimensional optical sensor, the processing circuitry (which may be, for example, a digital signal processor (DSP)) can verify a type of tissue captured in the image (e.g., artery versus non-artery), which is a capability that conventional sensor devices in wearable devices are unable to provide, due to the one-dimensional nature of the optical sensors therein. Further, the sensor device described herein can detect correct placement of the sensor device with respect to an artery (or vein), can detect a distance from the sensor device to the skin surface, and is resistant to motion and discards motion artifacts.

Further, the sensor device described herein can be manufactured through use of common off the shelf (COTS) equipment and can be integrated into consumer-level devices such as wearable devices, mobile telephones, and the like. For instance, the multidimensional optical sensor can be a relatively low resolution, high frame rate spatial CMOS sensor, and can be coupled with a DSP that is configured to process image data captured by the multidimensional optical sensor in real-time. Due to the low but spatial resolution of the optical sensor, processing performed on generated images can be undertaken on-chip using conventional chip architectures and processing algorithms.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIGS. 11-15 illustrate exemplary devices that can include a sensor device.

DETAILED DESCRIPTION

Figure 1:
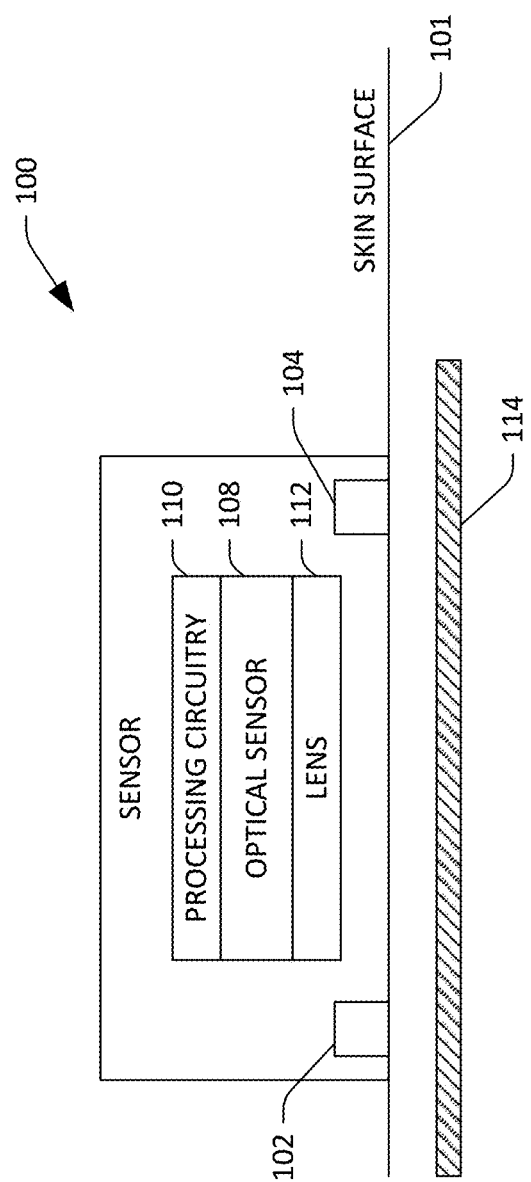
FIG. 1 is a schematic illustrating an exemplary sensor device that is configured to output data that is indicative of hemodynamics of a user.

Various technologies pertaining to a sensor device that is configured to output values that are indicative of multiple hemodynamics of a user are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B: or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

Described herein are various technologies pertaining to a sensor device that is configured to output data that is indicative of various health metrics with respect to a user including, but not limited to, arterial heart rate, arterial pulse wave velocity, pulse transit time, arterial expansion, arterial blood volume, pulse waveform, arterial diameter, arterial stiffness, tissue pulse rate, arterial blood oxygenation, and tissue oxygenation. Further, as will be described herein, the sensor device is non-invasive and can output the aforementioned data with the sensor device being placed at a single location on the body of the user (such as the wrist, arm, etc.).

With reference now to FIG. 1, a schematic of an exemplary sensor device 100 is illustrated. The sensor device 100 can be placed directly on or proximate to (e.g., within 10 mm) a skin surface 101 of a user. Further, as will be described in greater detail below, the sensor device 100 may be incorporated into a consumer-level device such as a fitness band, a smart watch, an arm band, a mobile telephone, or the like. In yet another exemplary embodiment, the sensor device 100 may be incorporated into a system in an ambulatory setting, such as a walk-in clinic or a pharmacy, where the user can place the sensor device 100 on the skin surface 101 and obtain values that are indicative of hemodynamics of the user.

The sensor device 100 includes illuminators 102 and 104, which are configured to emit light towards tissue beneath the skin surface 101 of the user. For example, the illuminators 102 and 104 may be light emitting diodes (LEDs) or any other suitable illuminators. Further, the illuminators 102 and 104 can emit light in the visible and/or near infrared spectrum. Thus, the illuminator 102 can emit light in the visible spectrum (e.g., having a wavelength corresponding to red or green light), while the illuminator 104 can emit light in the near infrared spectrum. Additionally, the illuminators 102 and 104 can be configured to emit visible and near infrared light at alternating times, such that when the illuminator 102 is emitting visible light the illuminator 104 fails to emit near infrared light, and while the illuminator 104 emits near infrared light the illuminator 102 fails to emit visible light. In another example, the sensor device 100 may include a single illuminator that emits light in one of the visible or near infrared spectrums. In still yet another example, the sensor device 100 can include multiple illuminators that emit visible light and/or multiple illuminators that emit near infrared light. To mitigate light emitted by the illuminators 102 and 104 from reflecting off the skin surface 106, the sensor device 100, in operation, can be positioned on the skin surface 101 such that the illuminators 102 and 104 are in contact with the skin surface 101. In such an embodiment, light emitted by the illuminators 102 and 104 couples directly into the skin rather than reflecting from the skin. Other exemplary embodiments will be described in greater detail below.

The sensor device 100 also includes a multidimensional optical sensor 108 that is configured to generate images, wherein a field of view of the optical sensor 108 is directed towards the skin surface 106 of the user. The optical sensor 108 can generate M×N pixel images, wherein both M and N are greater than 10, and further wherein M can be (but need not be) equivalent to N. In an example, the optical sensor 108 can be a complementary metal oxide semiconductor (CMOS) sensor, a charge coupled device (CCD) sensor, or the like. Accordingly, the optical sensor 108 includes an array of photodiodes, where charge can be read from the photodiodes to generate the M×N pixel images.

The sensor device 100 also includes processing circuitry 110 that is in communication with the optical sensor 108. For example, the processing circuitry 110 may be or include a digital signal processor (DSP) that is coupled to the optical sensor 108. In another example, the processing circuitry 110 can be or include an application specific integrated circuit (ASIC) that is on-chip with the optical sensor 108. In still yet another example, the processing circuitry 110 may be a general-purpose processor, such as one found in a mobile telephone. Summarily, the processing circuitry 110 is configured to receive images generated by the optical sensor 108 and generate and output data that is indicative of hemodynamics of the user based upon such images. More specifically, the processing circuitry 110, based upon images generated by the optical sensor 108, can generate and output values that are indicative of arterial heart rate, arterial pulse wave velocity, pulse transit time, arterial expansion, arterial blood volume, pulse waveform, arterial diameter, arterial stiffness, tissue pulse rate, arterial blood oxygenation, and tissue oxygenation. Operation of the processing circuitry 110 when generating such values will be described in greater detail herein.

The sensor device 100 may also optionally include a lens 112 that is optically coupled to the optical sensor 108, wherein the lens 112 has a focal point that is beneath the skin surface 101 of the user. The lens 112 defines a field of view of the optical sensor 108. The sensor device 100 may optionally be or include a Contact Image Sensor, wherein the pixel sensors are placed in direct contact with the skin and don't require a lens or lenses as a focusing device.

While the schematic depicted in FIG. 1 illustrates one exemplary implementation of the sensor device 100, other embodiments are also contemplated. For example, the illuminants 102 and 104 may be included in the processing circuitry 110. In such an embodiment, the sensor device 100 may include prisms and/or lenses that are configured to direct light emitted by such illuminants 102-104 towards the skin surface 101, such that at least some of the light penetrates the skin surface 101. Further, while the optical sensor 108 has been described as being a CMOS or CCD sensor, other technologies for generating images are also contemplated. The optical sensor 108 can include an array of photodiodes surrounded by light emitters (e.g. LEDs). In yet another example, the optical sensor 108 can include an array of LEDs, some of which may be operated in reverse as photodiodes. In still yet another example, the optical sensor 108 may be a contact image sensor. Other implementations are also contemplated.

Exemplary operation of the sensor device 100 is now set forth. The sensor device 100 is placed upon the skin surface 101 of the user such that, for example, an artery 114 of the user is within a field of view of the optical sensor 108. When the sensor device 100 is placed upon the skin surface 101 of the user, the optical sensor 108 generates images, and the processing circuitry determines whether the artery 114 is captured in the images. When the processing circuitry 110 is unable to identify the artery 114, or when the artery 114 is not positioned near the center of images generated by the optical sensor 108, the processing circuitry 110 can cause a notification to be provided to the user, instructing the user to move the sensor device 100 over the skin surface 101 until the artery 114 is approximately at the center of images generated by the optical sensor 108. While the optical sensor 108 is capturing images, the illuminators 102 and 104 inject light into the skin surface 101, such that dermis in the field of view of the optical sensor 108 is illuminated. The light emitted by the illuminants 102 and 104 enters the skin and gets diffused and/or absorbed, depending on the spectral reflecting characteristics of the dermis, the matter in the subdermal area, and the artery 114 (including oxygenated and deoxygenated blood), and the optical sensor 108 generates images based upon detected reflected light. The processing circuitry 110 can determine a distance between the lens 112 and the skin surface 101, and can adjust a focal point of the lens 112 such that it corresponds to the location of the subdermal arteries (e.g., the artery 114) beneath the skin surface 101, and the arteries appear in focus in the images generated by the optical sensor 108. It is to be noted that the distance remains constant, and the processing circuitry 110 need not recalibrate or require adjustment by the user once initially calibrated and position-adjusted.

Blood carried through the artery 114 absorbs light emitted by the illuminants 102 and 104, while other parts of subdermal tissue reflect light emitted by the illuminants 102 and 104. The result is that an image generated by the optical sensor 108 (when the artery 114 is in the field of view of such sensor 108) includes a region corresponding to the artery 114 that is darker than other regions of the image.

The optical sensor 108 can generate images at a relatively high frame rate (e.g., 1200 fps), and the processing circuitry 110 can continuously process images generated by the optical sensor 108 to compute and output values that are indicative of hemodynamics of the user based upon the images. Further, the processing circuitry 110 can utilize noise reduction techniques and/or image enhancement processes with respect to images generated by the optical sensor 108 to facilitate computing and outputting the values that are indicative of the spatial hemodynamics of the user. Further, as will be described below, the processing circuitry 110 can validate spatial hemodynamics generated by the processing circuitry 110 based upon analysis of the images generated by the optical sensor 108.

Figure 2:
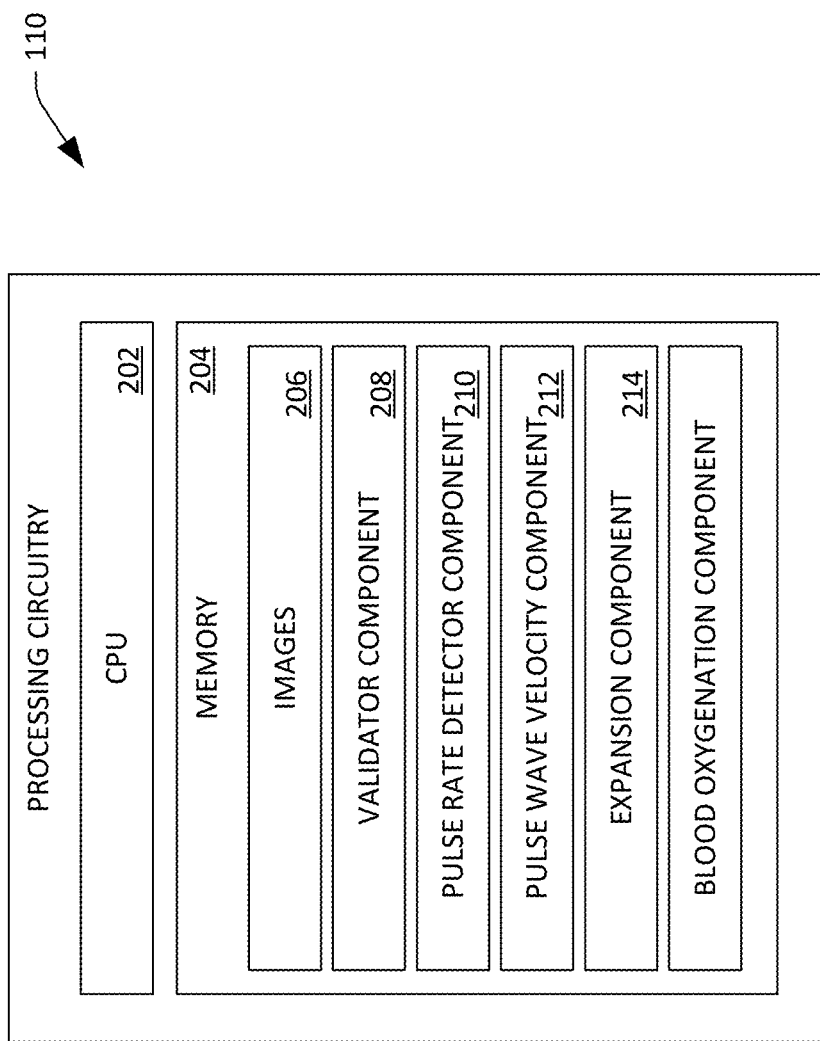
FIG. 2 is a functional block diagram of exemplary processing circuitry that is configured to compute values that are indicative of hemodynamics of a user.
Figure 3:
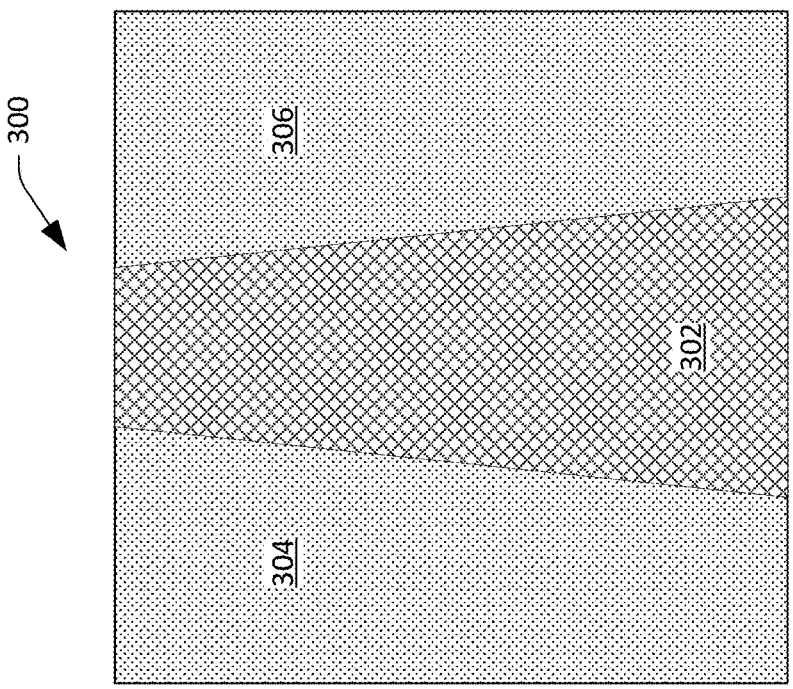
FIG. 3 depicts an exemplary image that can be generated by a multidimensional optical sensor.

Now referring to FIG. 2, a functional block diagram of the processing circuitry 110 is illustrated. As noted above, the processing circuitry 110 may be a DSP that has a central processing unit (CPU) 202 and associated memory 204. The processing circuitry 110 may alternatively be an ASIC, a field programmable gate array (FPGA), or other suitable processing circuitry. In the example shown in FIG. 2, the memory 204 includes images 206 generated by the multi-dimensional optical sensor 108. The memory 204 also includes a validator component 208 that is configured to analyze each image in the images 206 to ascertain whether the artery 114 is observable in the image. Referring briefly to FIG. 3, an exemplary image 300 that can be generated by the optical sensor 108 is depicted. It is to be understood that the image 300 is presented for purposes of describing an exemplary operation of the processing circuitry 110, and is not intended to limit operation of the processing circuitry 110 to the image 300. For example, while the image 300 depicts a dark region that tapers and runs vertically across the image 300, the processing circuitry 110 can function when dark regions have different orientations with respect to boundaries of images and when dark regions have different shapes from what is depicted in the image 300. As indicated above, the image 300 includes a dark region 302 that runs vertically across the image 300, while other regions 304 and 306 that surround the dark region 302 are lighter. As blood absorbs light emitted by the illuminators 102 and 104, the dark region 302 represents the artery 114 while the regions 304 and 306 represent subdermal tissue (other than the artery 114). While the dark region 302 is shown as travelling vertically through the image 300, in most scenarios a dark region corresponding to an artery will pass diagonally in some way through an image generated by the optical sensor 108.

Figure 4:
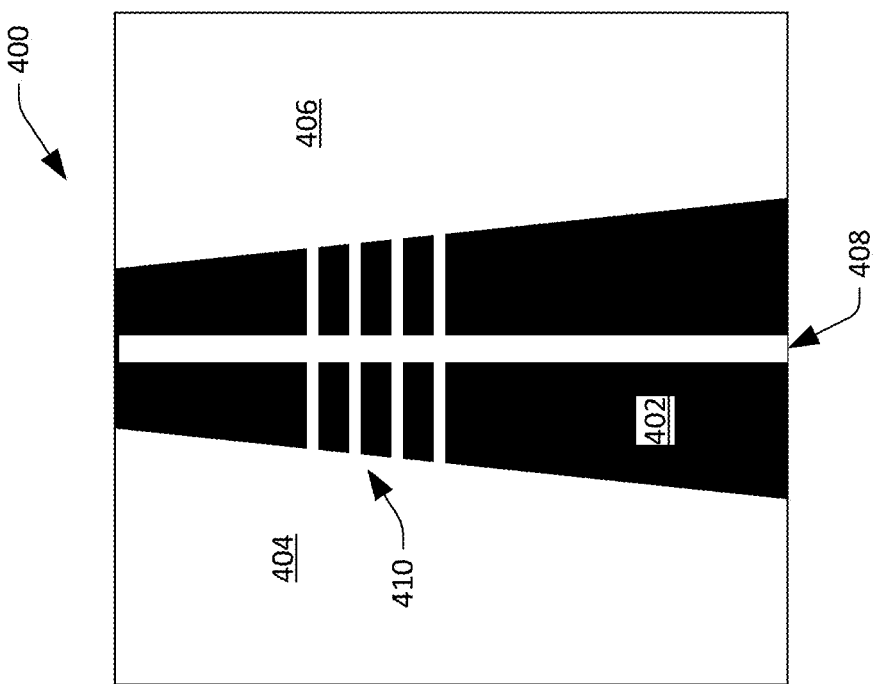
FIG. 4 depicts the exemplary image depicted in FIG. 3 after processing has been undertaken on such image to enhance contrast.

Now referring to FIG. 4, an image 400 is depicted, wherein the processing circuitry 110 can generate the image 400 based upon the image 300. For instance, the validator component 208 can perform tone mapping on the image 300 to maximize contrast in the image, thereby clearly differentiating the artery 114 from other subdermal tissue in the image 400. Accordingly, the image 400 includes a dark region 402 that represents the artery 114 and light regions 404 and 406 that represent other subdermal tissue. As noted previously, an image may also include a dark region that represents a vein (as the vein carries blood). Further, the validator component 208 can perform bicubic interpolation (e.g., by a factor of 100) on the image 300 to delineate boundaries of the dark region 402 in the image 400.

The validator component 208 can further identify direction of the artery 114 in the image 400 as well as (relative) width of the artery 114 at different locations along the artery 114. The direction of the artery 114 is detected and represented (for illustration) in the image 114 by a white line 408 that extends vertically through the image 400. For example, the validator component 208 can ascertain a principle component of the dark region 402 and identify the direction of the artery 114 (e.g., the location of the white line 408 in the image 400) based upon the principal component of the dark region 402. In another example, the validator component 208 can identify the midpoint of the dark region 402 in the uppermost row of pixels in the image 400, and can identify the midpoint of the dark region 402 in the lowermost row of pixels in the image 400, and can ascertain the direction of the artery 114 by connecting the midpoints. In still yet another example, the validator component 208 can employ Hough line analysis to determine the direction of the artery 114 in the image 400.

The validator component 208 can also compute (relative) widths of the artery at different locations in the image. The validator component 208 can select a point along the white line 408 and then define a line that is perpendicular to the white line that extends to the boundaries of the dark region 402. The image 400 illustrates several horizontal white lines 410, which are perpendicular to the white line 408 and extend a width of the dark region 402. These lines, which represent relative widths of the artery 114 at different locations along the artery 114, are referred to herein as probe lines.

Returning to FIG. 2, the validator complement 208 validates each image in the images 206 by determining the following: 1) that there is a long dark region in the image surrounded by bright areas: 2) when there is a long dark region in the image, that the dark region is in focus (determined based upon the crispness of the exterior of the dark regions 402) and spans the whole sensor area; and 3) when the dark region is in focus and spans the sensor area, that sampled widths of the dark region are within an expected range (e.g., a number of pixels wide that generally correspond to a typical artery width, such as 2.5 mm). When the validator component 208 fails to validate an image, the image can be discarded such that the image is not employed to compute values that are indicative of hemodynamics of the user. Accordingly, the validator component 208 will detect motion artifacts in images and discard images that include motion artifacts. In such images, no sharp dark feature with an expected width would be ascertainable, and the validator component 208 will accordingly fail to validate the images. Similarly, when the sensor device 100 is not positioned above the artery 114, an image generated by the optical sensor 108 will fail to include a dark region with an expected width or will include an image that lacks a dark region with a requisite crispness (e.g., the image will be unfocused and therefore blurry). Therefore, the processing circuitry 110 refrains from outputting values that are indicative of hemodynamics of the user based upon images not validated by the validator component 208.

The memory 204 additionally includes a pulse rate detector component 210 that can be configured to detect heart rate and/or pulse waveform of the user based upon images generated by the optical sensor 108 and validated by the validator component 208. In an exemplary embodiment, the pulse rate detector component 210 can generate values that are indicative of the heart rate and/or pulse waveform by generating a time series of values based upon images generated by the optical sensor 108. For instance, for each image generated by the optical sensor 108 and validated by the validator component 208, the pulse rate detector component 210 can compute a mean intensity value of pixels in the image. Since the sensor device 100 is located on top of the artery 114, reflections captured by the optical sensor 108 over time are a function of reflections from a combination of: 1) blood pushing through the artery 114; 2) blood flowing through the microvasculature that surrounds the artery 114 and 3) subtle motion artifacts of the sensor device 100. Thus, the average intensities across images captured over time is representative of an amount of blood flowing across subdermal tissue (including the artery 114) in the field of view of the optical sensor 108.

Figure 5:
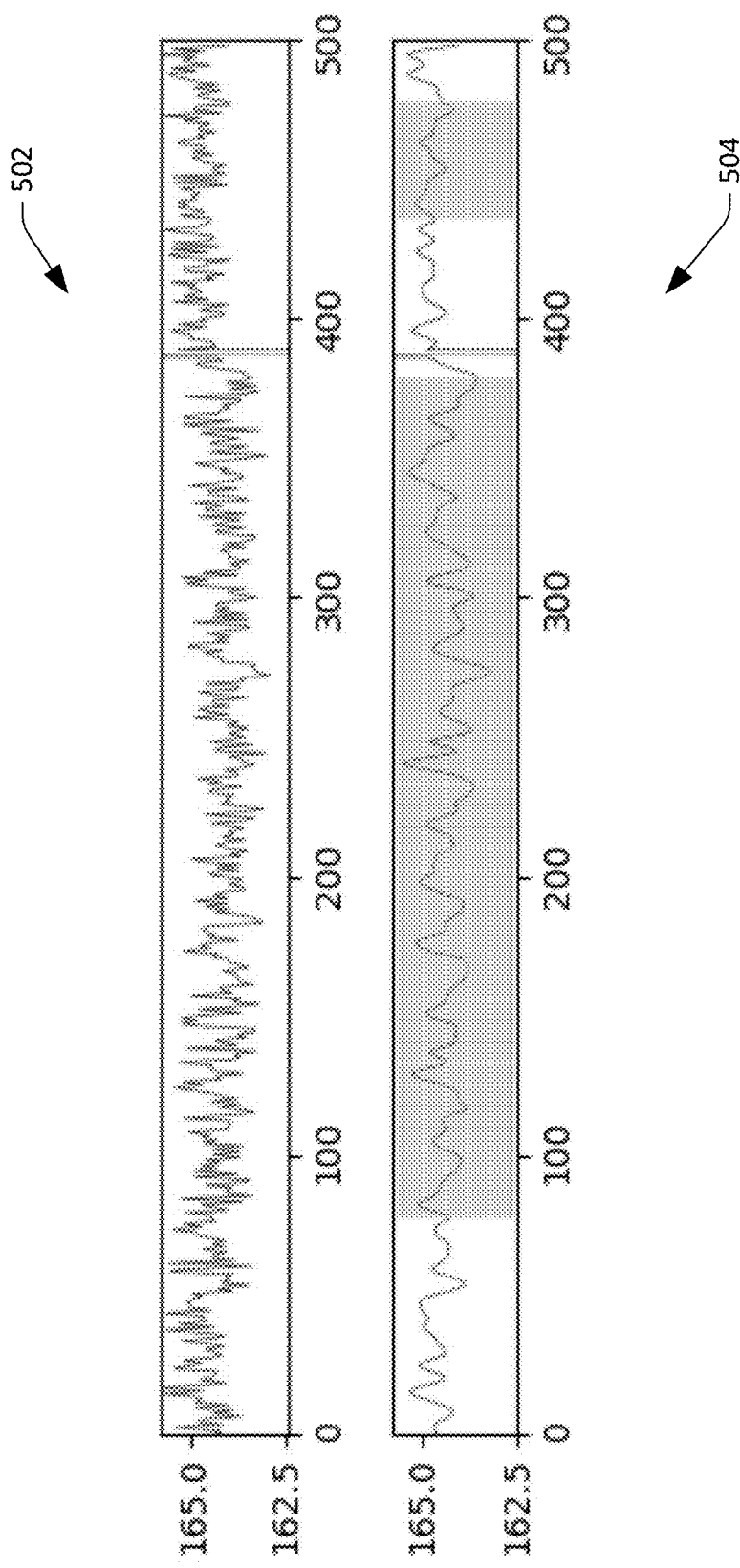
FIG. 5 depicts an exemplary waveform that can be generated based upon images captured by the multidimensional optical sensor.

Referring briefly to FIG. 5, plots 502 and 504 of waveforms that can be generated by the pulse rate detector component 210 are shown. The plots 502 and 504 are representative of mean intensities of (validated) images captured by the optical sensor 108 over time, wherein the plot 502 illustrates raw data and the plot 504 depicts a waveform generated by the pulse rate detector component 210 based upon the raw data shown in the plot 502, where the waveform is indicative of the pulse rate and the pulse waveform of the user. For instance, the pulse rate detector component 210 can execute a fast Fourier transform (FFT) over the raw data to generate the waveform shown in the plot 504. The pulse rate detector component 210 can identify peaks in the waveform, and measure inter-peak intervals to determine the pulse rate of the user. Additionally, the pulse rate detector component 210 can filter waveforms that do not correspond to an expected waveform shape and/or expected pulse rate (e.g., in situations where motion artifacts in captured images result in noise that may render the extracted waveform inaccurate).

Returning to FIG. 2, the memory 204 also includes a pulse wave velocity component 212 that is configured to compute pulse wave velocity and/or pulse transit time of the user based upon images generated by the optical sensor 108 and validated by the validator component 208. When computing pulse wave velocity and/or pulse transit time, the pulse wave velocity component 212 defines sampling regions in each (validated) image generated by the optical sensor 108. Put differently, as described above, the validator component 208 can identify walls of the artery 114 in each image. The pulse wave velocity component 212 can, for each validated image, define two sampling regions the correspond to two different locations along the artery 114 (e.g., where the sampling regions are separated by some threshold number of pixels). The pulse wave velocity component 212 can compute a mean intensity value for each sampling region in each image, and low-pass filter the mean intensities (resulting in a time series for each sampling region, where the time series is similar to that shown in FIG. 5).

Figure 6:
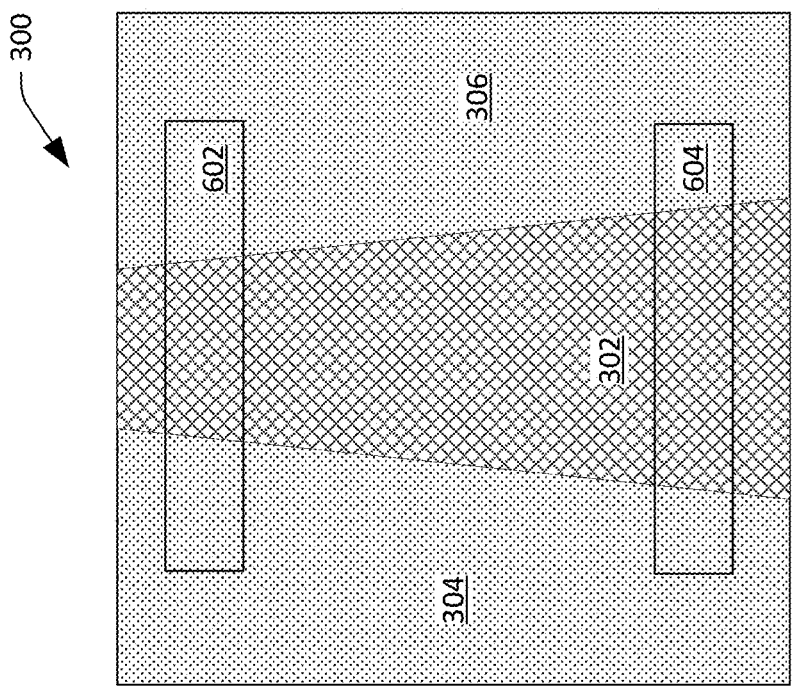
FIG. 6 depicts an image with two sampling regions illustrated, where the sampling regions are usable in connection with computing pulse wave velocity and pulse transit time of a user.

With reference to FIG. 6, the image 300 shown in FIG. 3 with two sampling regions 602 and 604 placed over portions of the image 300 that include the dark region 302 is illustrated. As blood flows through the artery 114, the artery will expand and contract. With respect to FIG. 6, when blood is flowing through the artery 114 downward in a vertical direction over time, the artery 114 initially expands in the sampling region 602 as it is filled with blood and contracts as blood exits the artery 114. As the blood continues to flow through the artery 114, the artery 114 contracts in the region 602 and expands in the region 604. As noted above, for each validated image generated by the optical sensor 208, the pulse wave velocity component 212 computes a mean intensity value for each of the regions 602 and 604, thereby creating two time-series: a first time-series for the region 602, and a second time-series for the region 604. The pulse wave velocity component 212 can low-pass filter these time-series, creating two waveforms, wherein the waveforms are indicative of expansion and contraction of the artery 114 over time at locations along the artery 114 that correspond to the sampling regions 602 and 604. One of the two waveforms will trail the other in time. Further, the pulse wave velocity component 212 can have knowledge of or compute the distance between the two sampling regions 602 and 604, as the distance is a function of features of the lens 112 and resolution of the optical sensor 108. The pulse wave velocity component 212 can compute the velocity of a pulse based upon temporal offsets between the two waveforms.

Figure 7:
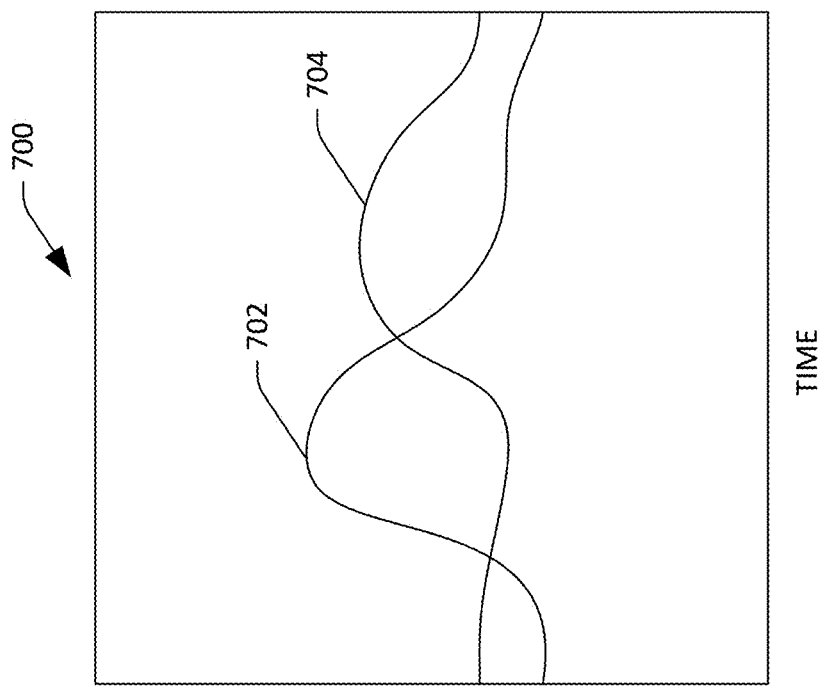
FIG. 7 depicts exemplary waveforms that can be generated based upon intensities of pixels in the sampling regions shown in FIG. 6.

Referring briefly to FIG. 7, a plot 700 illustrating a portion of two waveforms 702 and 704 with respect to time is illustrated. The waveform 702 is generated based upon mean intensities of the sampling region 602 of several images, while the waveform 704 is generated based mean intensities of the sample region 604 of the several images. Using the known distance between the locations on the artery 114 corresponding to the sampling regions 602 and 604, and the time between peaks in the waveforms 702 and 704, the pulse wave velocity component 212 can compute the velocity of the pulse as it travels through the artery 114. While FIG. 6 depicts the artery 114 being in a plane that is parallel with the sensor device 100, it is to be understood that the artery 114 may be at an angle or may be diagonal across the image 300; accordingly, the pulse wave velocity component 212 can compute the distance of the artery 114 between the two windows 602 and 604 along the white line 408 shown in FIG. 4.

Further, the pulse wave velocity component 212 can verify the quality of the computed pulse wave velocity prior to outputting a value that is indicative of the pulse wave velocity. For example, when there is not a high correlation between the waveforms 702 and 704, the pulse wave velocity component 212 can refrain from outputting a value that is indicative of pulse wave velocity.

Returning to FIG. 6, sizes of the windows 602 and 604 (and therefore a number of pixels in the windows 602 and 604) may be a function of the resolution of the optical sensor 108: the more pixels used by the pulse wave velocity component 212 to compute the pulse wave velocity, the more stable the signal becomes because noise is filtered out as larger sample windows are used. When the windows 602 and 604 are large, however, the pulse wave velocity component 212 may contemplate data about the tissue vasculature as well as larger stretches of the artery 114. Ideally, for each of the windows 602 and 604, intensities are sampled at exactly one location of the artery 114 (e.g., one vertical row of an image assuming that the artery 114 runs vertically, as in FIG. 3). The pulse wave velocity component 212 can compute the pulse transit time based upon the difference of temporal features between the waveforms 702 and 704, and can be converted to pulse wave velocity based upon distance along the white line 408 between the sampling windows 702 and 704.

Returning again to FIG. 2, the memory 204 also includes an expansion component 214 that is configured to compute values that are indicative of arterial expansion and/or blood volume based upon the (validated) images generated by the optical sensor 108. Returning to FIG. 4, the expansion component 214 can employ one or more of the probe lines 410 (the horizontal lines that represent the width of the artery 114) as a type of logical sensor to compute values that are indicative of arterial expansion and/or blood volume. For example, the expansion component 214 can determine a length of one of the probe lines in each validated image generated by the optical sensor 108 to generate a timeseries. In another example, the expansion component 214 can determine lengths of all probe lines 410 in each image (where the probe lines are proximate to one another in each of the images), and can average the lengths to generate a timeseries.

Figure 8:
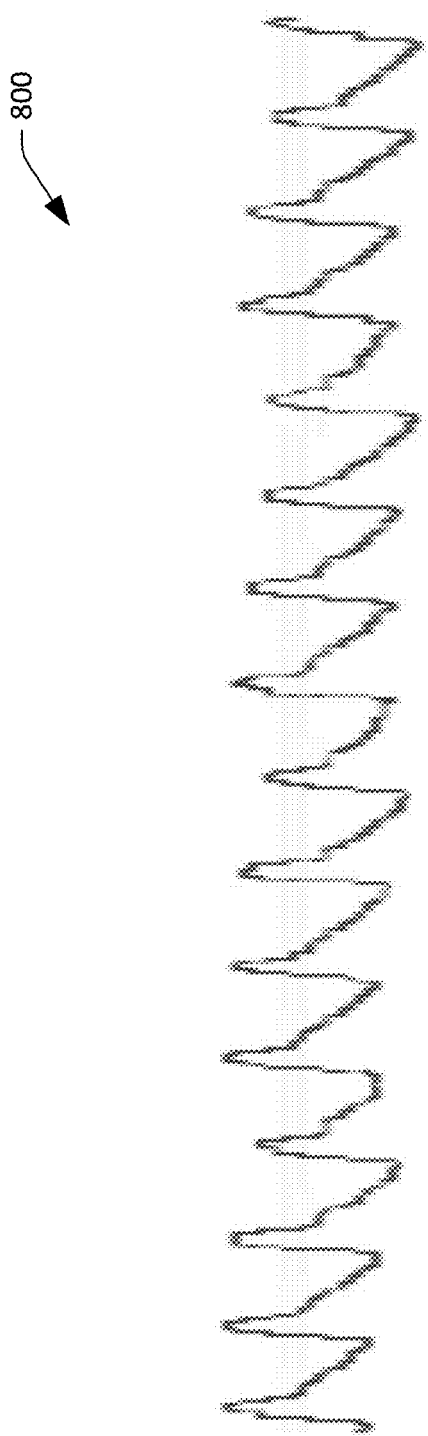
FIG. 8 illustrates a waveform that depicts expansion and contraction of an artery over time, wherein such waveform can be generated based upon images captured by the multidimensional optical sensor.

FIG. 8 depicts an exemplary timeseries 800 that represents expansion and contraction of probe lines over time in images generated by the optical sensor 108. It is to be noted that the timeseries 800 does not result from bare reflections in the images generated by the optical sensor 108, but instead represents physiological features that are present in the artery 114 at the site of the probe lines 410. The peaks in the timeseries 800 correspond to arterial expansion at peak pressure (systolic pressure), whereas the troughs in the timeseries 800 correspond to diastolic pressure after a pulse wave of blood has rushed through this part of the artery 114. Unlike the above-described reflection-based time series, the relative changes are physiologically significant and indicate the minimum and maximum expansion of the artery 114 at the location of the probe lines 410.

Figure 9:
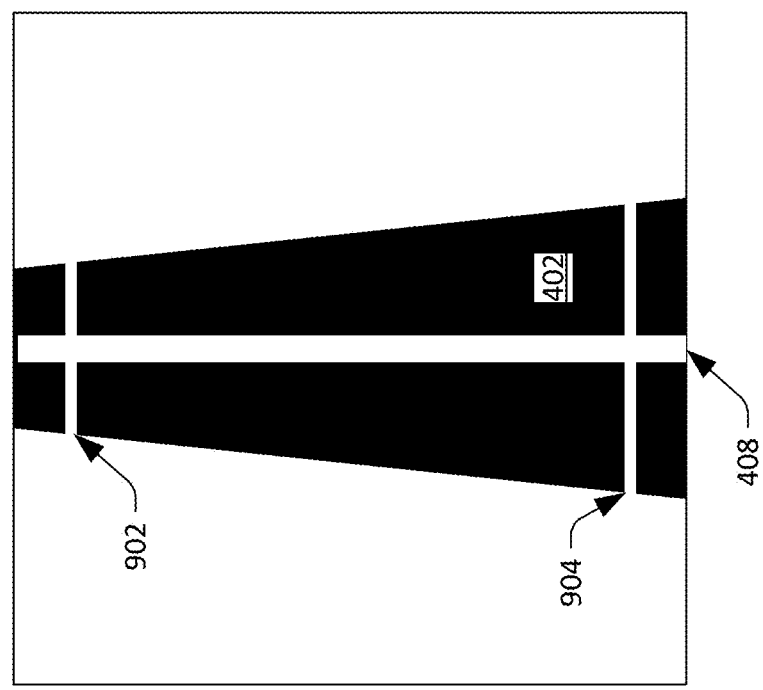
FIG. 9 illustrates probe lines through a diameter of an artery, wherein altering lengths of the probe lines over time can be analyzed to compute a value that is indicative of pulse wave velocity a user and/or pulse transit time for the user.

The expansion component 214 can also generate an indication of pulse transit time and/or pulse wave velocity based upon changing widths of probe lines (at two different locations) over time. For instance, the expansion component 214 can, for each validated image generated by the optical sensor 108, determine a width of two probe lines (e.g., a first probe line at the top of the image 400 and a second probe line at a bottom of the image 400). The expansion and contraction of two different probe lines at two different locations in images generated by the optical sensor 108 will follow each other in time as blood rushes through the artery 114. Referring to FIG. 9, an exemplary image 900 includes a first probe line 902 and a second probe line 904 at different locations along the white line 408 through the dark region 402. The expansion component 214 can record the lengths of the probe lines 902 and 904 over time. Further, the expansion component 214 can record lengths of probe lines (not shown) that are proximate to the probe lines 902 and 904, respectively, average the lengths, and generate two time-series. When blood flows through the artery 114 (e.g., vertically downward), the probe line 902 initially expands while the probe line 904 contracts, and subsequently as the blood rushes through the artery 114 the probe line 902 contracts while the probe line 904 expands. As noted above, the expansion component 214 can generate two timeseries, which will have corresponding peaks and troughs that are temporally offset from one another, wherein the expansion component 214 can use the temporal offset and the distance between the probe lines 902 at 904 (and thus the distance between the locations on the artery 114 represented by the probe lines 902-904) to estimate pulse wave velocity and/or pulse transit time. The expansion component 214, thus, can estimate the pulse wave velocity as a function of the expansion and contraction of the artery 114 itself, thereby modeling the pressure wave on the arterial wall.

The expansion component 214 can additionally compute a value that is indicative of blood volume/stroke volume by modeling the artery 114 as a tube with a known diameter, wherein the diameter can be estimated based upon: 1) the lengths of probe lines in the (validated) images 206; and 2) the pulse wave velocity. The length of the probe lines is indicative of the cross-sectional area of the artery 114, such that the blood volume flow rate results from $$Q = \frac{\text{Volume}}{\text{time}} = \text{Area} * \frac{pulsewidth}{\text{time}}.$$

Time intervals result from the update rates of the optical sensor 108, during which a single cross-section of the artery 114 can be assumed to be constant (e.g., reflecting the tube model during which the blood rushes at the detected speed that equals the pulse wave velocity at this time). Because liquids are incompressible, any portion of liquid flowing through a pipe could change shape but must maintain the same volume; this is true even if the pipe changes diameter (which is true in the case of the artery 114).

Referring again to FIG. 2, the memory 204 also comprises a blood oxygenation component 216 that is configured to compute both: 1) the arterial blood oxygenation; and 2) tissue oxygenation. Pursuant to an example, the illuminators 102 and 104 (FIG. 1) can be configured to emit light in different wavelengths, such as red and near infrared. The optical sensor 108 can be sensitive across these wavelengths, and the blood oxygenation component 216 can determine an amount of reflected light in terms of the relative differences in light intensities. In other words, the optical sensor 108 can generate a first image when the illuminator 102 is emitting red light, and can generate a second image when the illuminator 104 is emitting near infrared light. The blood oxygenation component 216 can determine the blood oxygenation based upon differences in mean intensities of the two images; thus, the blood oxygenation component 216 can compute blood oxygenation using conventional techniques.

What distinguishes the sensor device 100 over conventional devices is its ability to distinguish and compare blood oxidation inside the artery 114 (e.g., peripheral arterial oxygenation $SpO_2$) and in the microvasculature (e.g., tissue oxygenation $StO_2$). Thus, the blood oxygenation component 216 can determine the quality of perfusion and oxygen transported to the tissue. This is something current devices are incapable of, as current devices simply report the oxygen saturation in a part of the body a sensor happens to sit on. Accordingly, conventional devices (such as fitness bands with blood oxygenation sensing capabilities), when reporting blood oxygenation, may report a mixture of arterial oxygenation as well as oxygenation the microvasculature due imprecise positioning that cannot be calibrated to an arm of each and every wearer.

Figure 10:
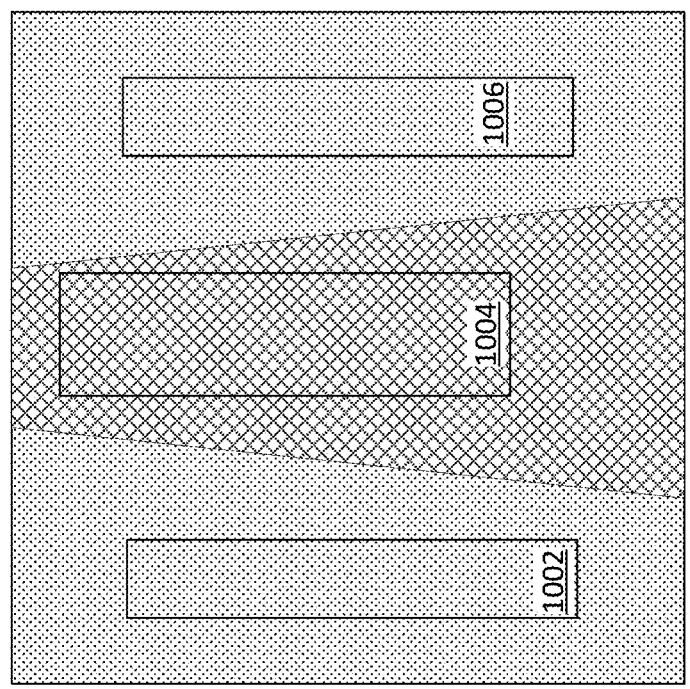
FIG. 10 depicts an image with sampling regions overlaid thereon that can be employed to compute values that are indicative of arterial blood oxygenation and tissue blood oxygenation.

The blood oxygenation component 216 distinguishes between arteries and the surrounding tissue and microvasculature. Referring now to FIG. 10, the image 300 is illustrated with three sample windows 1002-1006 overlaid thereon. In more detail, the validator component 208 can identify the boundaries of the artery 114 in the image 300, and the blood oxygenation component 216 can place the sample window 1004 over a region of the image 300 that only represents the artery 114. Similarly, the blood oxygenation component 216 can place the sample windows 1002 and 1006 over regions of the image 300 that represent the microvasculature (and not the artery 114). The blood oxygenation component 216 can then employ the conventional approach within each sample window to compute the blood oxygenation for each sample window (one for blood oxygenation inside the artery 114 based upon pixel intensity values in the sample window 1004 and one for blood oxygenation in the microvasculature based upon the pixel intensity values in the sample windows 1002 and 1006). When the validator component 208 fails to identify an artery in an image, the blood oxygenation component 216 can compute a single value for blood oxygenation.

FIGS. 11-15 depict different device form factors that can incorporate the sensor device 100. When the sensor device 100 is placed on a part of a body with the processing described above, even when the validator component 208 is unable to identify an artery, the sensor device 100 can output values that are indicative of heart rate, pulse transit time, blood oxygenation, etc. based on optical reflections. When the validator component 208 identifies the artery 114, the sensor device 100 can also generate and output values that are indicative of pulse transit time, pulse wave velocity blood volume, and the like using spatial image processing.

Figure 11:
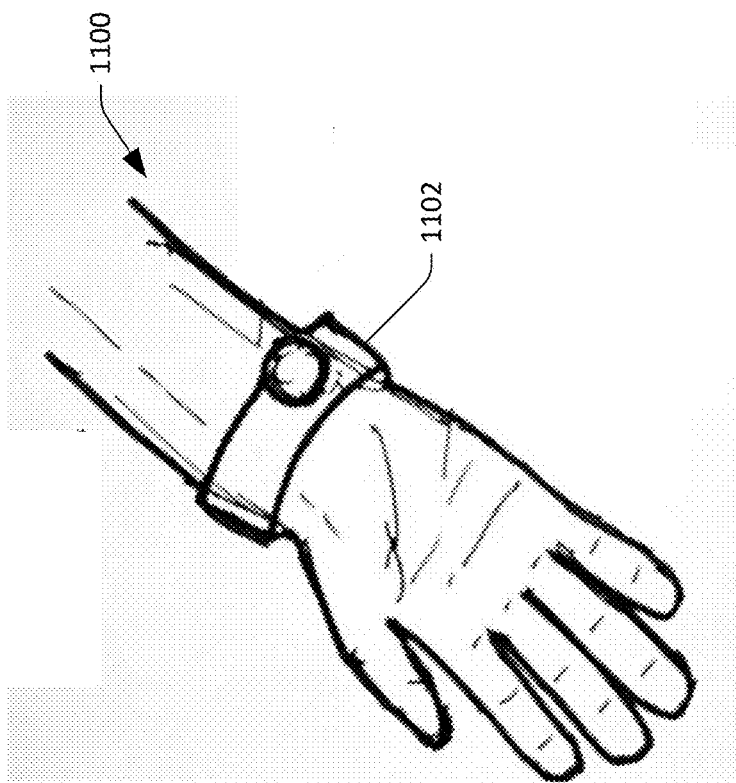

Referring solely to FIG. 11, an illustration 1100 of an exemplary device into which the sensor device 100 can be incorporated is shown. The sensor device 100 can be incorporated into a watch (or fitness band) 1102, which is worn around a wrist of the user. In such an embodiment, the sensor device 100 may be desirably positioned over the ulnar artery. The ulnar artery is a main blood vessel, with oxygenated blood, of the medial aspect of the forearm. The ulnar artery arises from the brachial artery and terminates in the superficial palmar arch, which joins with the superficial branch of the radial artery. The ulnar artery is palpable on the interior of and medial aspect of the wrist. In another example, the sensor device 100, when placed in a watch as shown in FIG. 11, can be positioned over the radial artery (the main artery of the lateral aspect of the forearm), which lies superficially in front of the distal end of the radius (e.g., such that the sensor device 100 is positioned on a lateral aspect of the wrist). The radial artery is typically the artery used by clinicians when taking a radial pulse.

Figure 12:
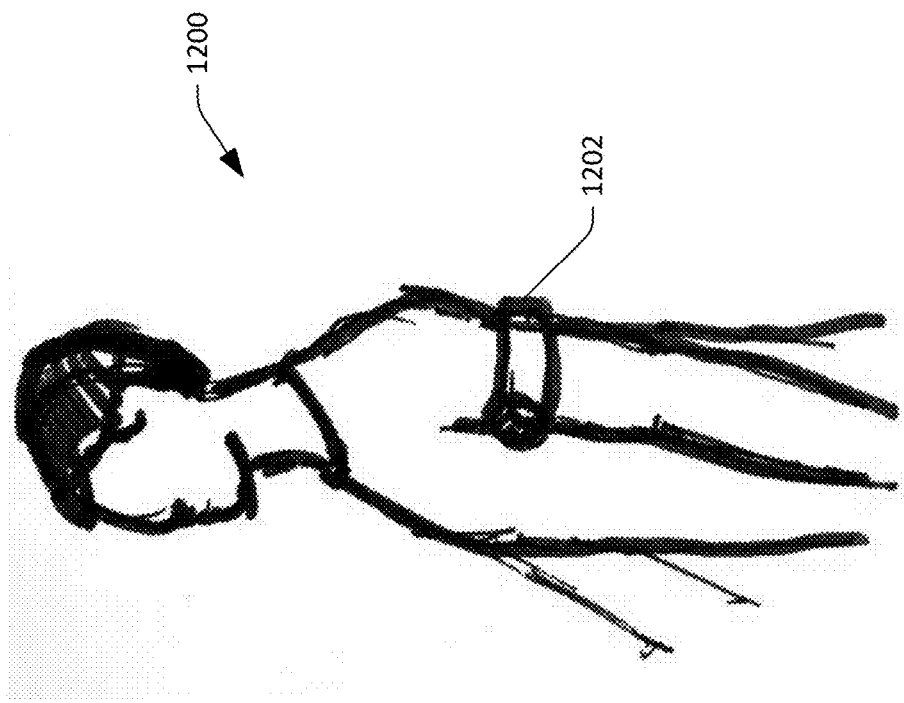

Now referring to FIG. 12, an illustration 1200 of another exemplary device into which the sensor device 100 can be incorporated is depicted. An arm strap 1202 may incorporate the sensor device 100 such that the sensor device 100, when the arm strap 1202 is worn by a user, is placed over a major blood vessel of the upper arm (the brachial artery). The pulse of the brachial artery is palpable on the anterior aspect of the elbow, medial to the tendon of the biceps, and, with the use of a stethoscope and sphygmomanometer (blood pressure cuff) often used to measure the blood pressure.

Figure 13:
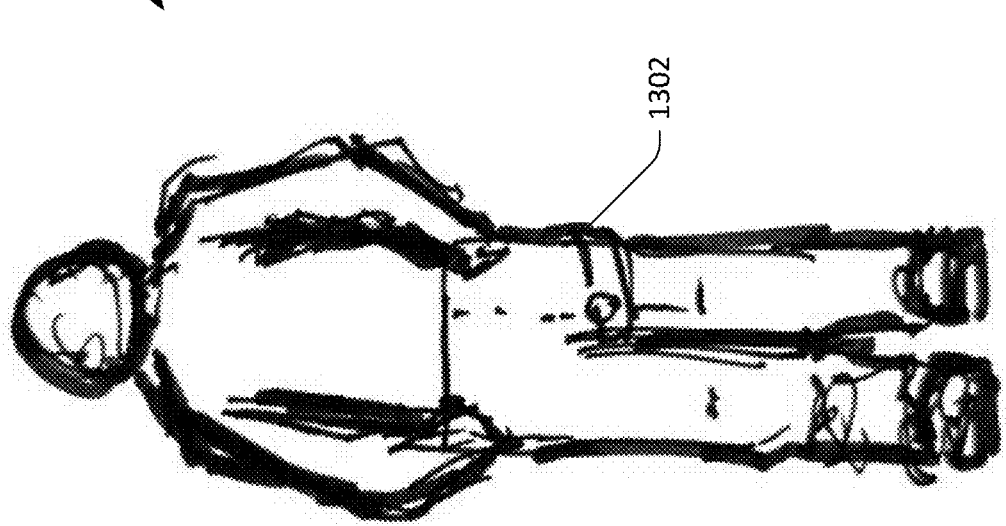

With reference now to FIG. 13, an illustration 1300 of yet another exemplary device into which the sensor device 100 can be incorporated is shown. The sensor device 100 can be incorporated into a leg strap that is to be worn around a leg of a user (underneath clothing), such that the sensor device 100 is positioned above the femoral artery. The femoral artery is the main arterial supply to the lower limb. The femoral artery can often be palpated through the skin, and is often used as a catheter access artery. The site for optimally palpating the femoral pulse is in the inner thigh.

Figure 14:
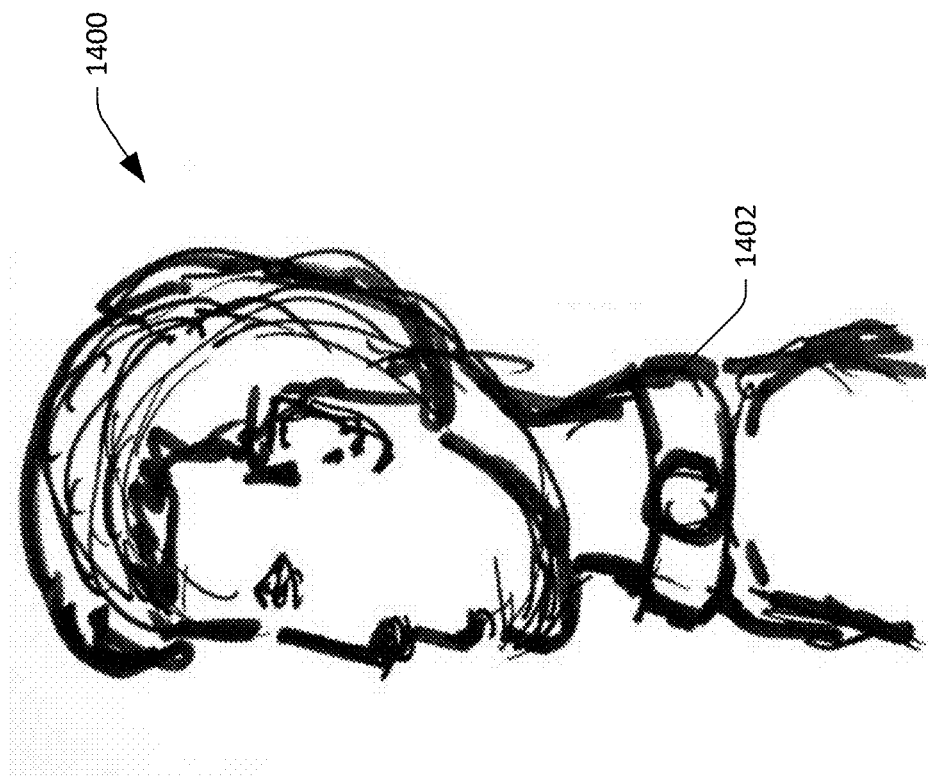

Now referring to FIG. 14 an illustration 1400 of still yet another exemplary device into which the sensor device 100 can be incorporated is shown. The sensor device 100 can be incorporated into a neck band 1402 positioned around a neck of a user, such that the sensor device 100 is positioned over the carotid artery. The carotid artery supplies the head and neck with oxygenated blood. The carotid artery is often used in measuring the pulse, especially in patients who are in shock and who lack a detectable pulse in the more peripheral arteries of the body.

Turning to FIG. 15, an illustration 1500 of another exemplary device into which the sensor device 100 can be incorporated is presented. The sensor device 100 can be incorporated into glasses 1502, such that the sensor device 100 is positioned over the superficial temporal artery. Additionally, the sensor device 100 can be incorporated into virtual reality goggles or other suitable head-mounted devices. The superficial temporal artery is a major artery of the head, and is often affected in giant-cell arteritis and biopsied if the diagnosis is suspected. Migraine attacks can occur when the temporal artery enlarges. As the sensor device 100 is configured to recognize artery enlargement, the sensor device 100 may serve as a monitor to detect migraine attacks.

Figure 16:
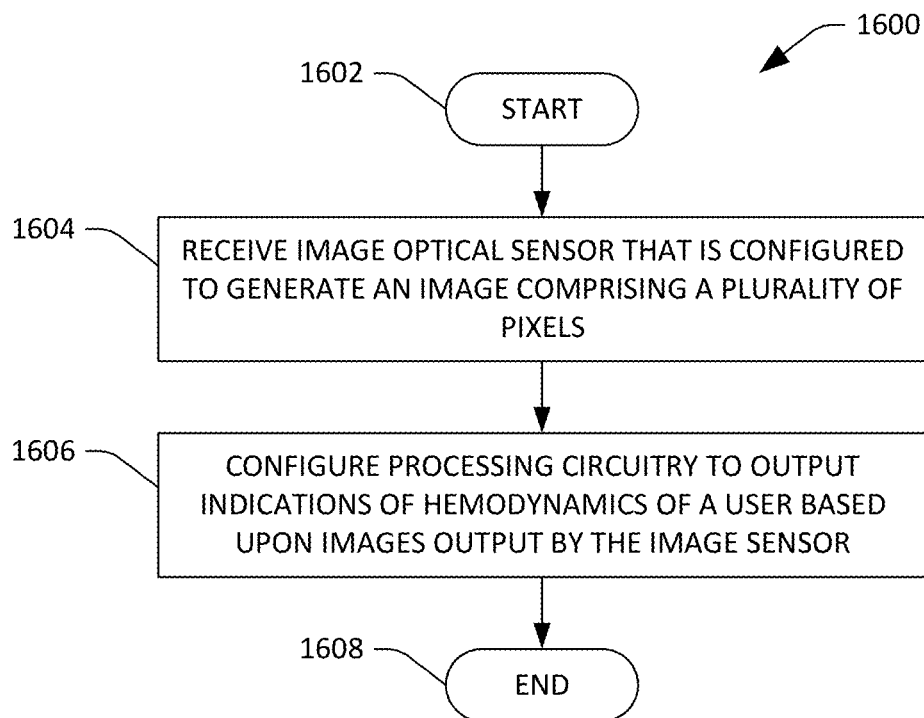
FIG. 16 is a flow diagram illustrates an exemplary methodology for constructing a sensor device that is configured to output data that is indicative of hemodynamics of a user.
Figure 17:
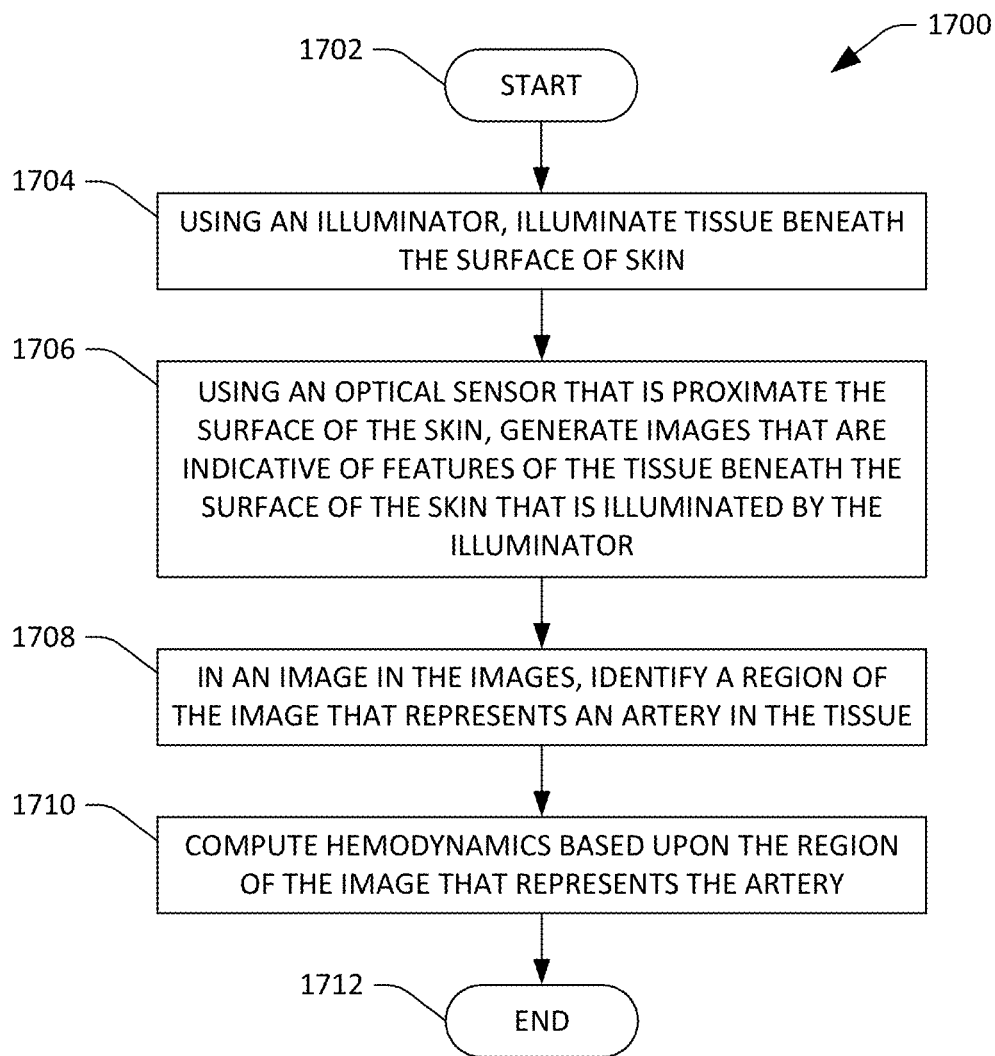
FIG. 17 is a flow diagram illustrating an exemplary methodology for computing hemodynamics of a user.

FIGS. 16 and 17 illustrate exemplary methodologies relating to a sensor device that is configured to output multiple hemodynamics of a user (including some hemodynamics that are spatial in nature). While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Now referring to solely to FIG. 16, an exemplary methodology 1600 for constructing a sensor device that is configured to compute multiple values that are indicative of hemodynamics of a user is illustrated. The methodology 1600 starts at 1602, and at 1604 an optical sensor is received. The optical image sensor is configured to generate images, wherein each of the images comprises a plurality of pixels (as described above). In an exemplary embodiment, the optical sensor may be a CMOS sensor. At 1606, processing circuitry is configured to output indications of multiple hemodynamics based upon images output by the optical sensor. For example, the processing circuitry can be configured to compute values that are indicative of at least two of: 1) arterial heart rate; 2) arterial blood oxygenation; 3) arterial pulse wave velocity; 4) arterial pulse transit time; 5) arterial diameter; 6) arterial expansion; 7) arterial pulse waveform; 8) arterial blood volume; 9) arterial stroke volume; 10) arterial stiffness; 11) tissue pulse rate; or 12) tissue oxygenation. In another example, the processing circuitry can be configured to output values that are indicative of three or more of such hemodynamics. In yet another example, the processing circuitry can be configured to output values are indicative of four or more of the aforementioned hemodynamics. In still yet another example, the processing circuitry can be configured to output indications of all of the hemodynamics referenced above. The methodology 1600 completes at 1608.

Now referring to FIG. 17, an exemplary methodology 1700 for operating a sensor device that is configured to output indications of spatial hemodynamics is illustrated. The methodology 1700 starts at 1702, and at 1704, using an illuminator (such as an LED), tissue beneath the surface of skin is illuminated, ideally above an artery. At 1706, using a multidimensional optical sensor that is positioned proximate the surface of the skin, images are generated that are indicative of features of the tissue beneath the surface of the skin that is illuminated by the illuminator. For instance, the images may capture an artery.

At 1708, in an image in the images, a region of the image that represents an artery in the tissue is identified. For example, each image generated by the optical sensor can be analyzed for a region that corresponds to an artery. At 1710, hemodynamics of the user are computed based upon the region of the image that represents the artery. The methodology 1700 completes at 1712.

Figure 18:
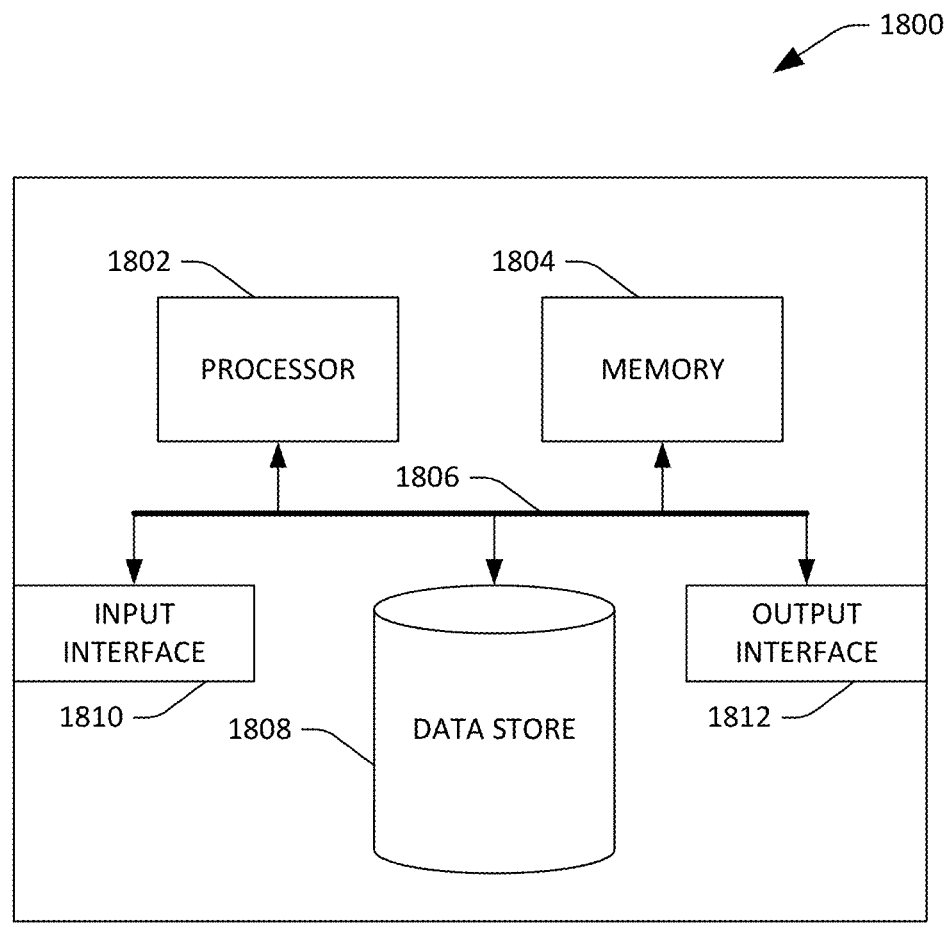
FIG. 18 is an exemplary computing system.

Referring now to FIG. 18, a high-level illustration of an exemplary computing device 1800 that can be used in accordance with the systems and methodologies disclosed herein is illustrated. For instance, the computing device 1800 may be used in a system that computes hemodynamics of a user. The computing device 1800 includes at least one processor 1802 that executes instructions that are stored in a memory 1804. The instructions may be, for instance, instructions for implementing functionality described as being carried out by one or more components discussed above or instructions for implementing one or more of the methods described above. The processor 1802 may access the memory 1804 by way of a system bus 1806. In addition to storing executable instructions, the memory 1804 may also store images generated by an optical sensor, threshold values, etc.

The computing device 1800 additionally includes a data store 1808 that is accessible by the processor 1802 by way of the system bus 1806. The data store 1808 may include executable instructions, images generated by an optical sensor, etc. The computing device 1800 also includes an input interface 1810 that allows external devices to communicate with the computing device 1800. For instance, the input interface 1810 may be used to receive instructions from an external computer device, from a user, etc. The computing device 1800 also includes an output interface 1812 that interfaces the computing device 1800 with one or more external devices. For example, the computing device 1800 may display text, images, etc. by way of the output interface 1812.

It is contemplated that the external devices that communicate with the computing device 1800 via the input interface 1810 and the output interface 1812 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 1800 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 1800 may be a distributed system. Thus, for instance, several devices may be in communication by way of a network connection and may collectively perform tasks described as being performed by the computing device 1800.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A wearable device that is configured to be placed on a portion of a body of a user, the wearable device comprising:
   a sensor device that is configured to output data that is indicative of hemodynamics of the user while the wearable device is positioned on the portion of the body of the user, wherein the sensor device is configured to:
      generate multi-dimensional images of an artery or vein of the user over time; and
      based upon the multi-dimensional images, compute and output values for at least two of the following:
      pulse transit time;
      arterial stiffness;
      arterial blood oxygenation; or
      tissue blood oxygenation.

2. The wearable device of claim 1 being a head-mounted device, wherein when worn by the user the sensor device is positioned over a superficial temporal artery.

3. The wearable device of claim 2, wherein the head-mounted device is glasses.

4. The wearable device of claim 1, wherein the sensor device comprises an array of illuminators that emit light in a non-visible spectrum and an array of detectors that detect light in the non-visible spectrum, wherein the images generated by the sensor device are based upon light emitted by the illuminators and light detected by the detectors.

5. The wearable device of claim 1, wherein the sensor device comprises an array of light emitting diodes (LEDs), wherein a first set of LEDs in the array are configured to emit light and a second set of LEDs in the array are operated as photodiodes and are configured to detect light, wherein the images are generated by the sensor device based upon light emitted by the first set of LEDs and light detected by the second set of LEDs.

6. The wearable device of claim 1, wherein the sensor device comprises:
   a multi-dimensional optical sensor that is configured to be positioned proximate to a surface of skin of the user and external to the portion of the body of the user, wherein the multi-dimensional optical sensor comprises an array of photodiodes and is configured to generate the multi-dimensional images; and
   processing circuitry that is in communication with the multi-dimensional optical sensor, wherein the processing circuitry is configured to:
      receive the multi-dimensional images generated by the multi-dimensional optical sensor; and
      validate, based upon the multi-dimensional images, that the multi-dimensional images include a region that corresponds to the artery or vein of the user, wherein the values are output responsive to validating that the multi-dimensional images include the region that corresponds to the artery or vein of the user.

7. The wearable device of claim 6, wherein the processing circuitry is further configured to identify a direction of the artery or the vein of the user, and further wherein the values are output based upon the identified direction of the artery or the vein as captured in the images received from the multi-dimensional optical sensor.

8. The wearable device of claim 1 being a wrist-wear.

9. The wearable device of claim 1, wherein the sensor device is further configured to output values for heart rate of the user and pulse wave velocity for the user.

10. A method performed by a wearable device when the wearable device is worn by a user on a portion of a body of the user, the method comprising:
    generating, by a sensor device in the wearable device, multi-dimensional images of an artery or vein of the user;
    outputting, by the wearable device, data that is indicative of hemodynamics of the user while the wearable device is worn by the user on the portion of the body of the user, wherein the device outputs the data based upon the multi-dimensional images generated by the sensor device, wherein the data includes values for at least two of the following:
    pulse transit time;
    arterial stiffness;
    arterial blood oxygenation; or
    tissue blood oxygenation.

11. The method of claim 10, wherein the wearable device is a head-mounted wearable device, and further wherein the sensor device, when the wearable device is worn on the portion of the body of the user, is positioned over a superficial temporal artery of the user.

12. The method of claim 11, wherein the head-mounted wearable device is glasses.

13. The method of claim 10, wherein the wearable device is worn on a wrist of the user.

14. The method of claim 10, wherein generating the multi-dimensional images of the artery or vein of the user comprises:
    emitting, by an illuminator of the sensor device, infrared light towards the portion of the body of the user to illuminate the artery or vein, wherein the multi-dimensional images are infrared images.

15. The method of claim 10, wherein generating the multi-dimensional images of the artery or vein of the user comprises:
    emitting, by an illuminator of the sensor device, visible light towards the portion of the body of the user to illuminate the artery or vein, wherein the multi-dimensional images are generated based upon the artery or vein being illuminated by the visible light.

16. The method of claim 10, wherein outputting the data comprises:

identifying a direction of the artery or the vein of the user in the images, wherein the data is output based upon the identified direction of the artery or the vein of the user in the images.

17. The method of claim 10, wherein generating the multi-dimensional images of the artery or vein of the user comprises generating the images through use of an array of devices, wherein the array of devices comprises both illuminators and photodetectors.

18. A wearable device that is configured to be worn by a user, the wearable device comprising:
- a multi-dimensional optical sensor that is configured to generate images of an artery or vein of the user when the wearable device is worn by the user, wherein the images have M x N pixels, where both M and N are greater than one; and
- processing circuitry that is configured to output values for hemodynamics of the user based upon the images of the artery or vein of the user, wherein the processing circuitry is configured to output the values while the wearable device is worn by the user, and further wherein the values comprise at least two of the following:
  - pulse transit time;
  - arterial stiffness;
  - arterial blood oxygenation; or
  - tissue blood oxygenation.

19. The wearable device of claim 18 being a watch.

20. The wearable device of claim 18 being headgear.

* * * * *